United States Patent [19]

Cassou et al.

[11] Patent Number: 4,846,785

[45] Date of Patent: Jul. 11, 1989

[54] INSTRUMENT FOR ARTIFICIAL INSEMINATION, EMBRYO TRANSFER OR SAMPLING FOLLICULAR LIQUIDS IN MAMMALS

[76] Inventors: Robert Cassou, Rue Clemenceau; Bertrand Cassou, Saint Symphorien des Bruyeres; Maurice Cassou, Rue Clemenceau, all of 61300 L'Aigle, France

[21] Appl. No.: 71,459

[22] Filed: Jan. 20, 1988

[30] Foreign Application Priority Data

Jan. 22, 1987 [FR] France ............................... 87 00711

[51] Int. Cl.[4] ............................................ A61M 37/02

[52] U.S. Cl. ........................................ 600/34; 600/35; 604/55; 604/224; 604/198

[58] Field of Search ................ 604/55, 159, 192, 198, 604/211, 224, 218; 600/34, 35

[56] References Cited

U.S. PATENT DOCUMENTS

| | | | |
|---|---|---|---|
| 1,718,596 | 6/1929 | Smith | 604/223 |
| 3,073,306 | 1/1963 | Linder | 604/198 |
| 3,756,240 | 9/1973 | Fuchslocher et al. | 604/224 |
| 4,173,227 | 11/1979 | Cassou et al. | 604/218 |
| 4,432,753 | 2/1984 | Cassou et al. | 604/55 |
| 4,642,094 | 2/1987 | North et al. | 604/55 |
| 4,702,739 | 10/1987 | Milorad | 604/198 |

FOREIGN PATENT DOCUMENTS

| | | |
|---|---|---|
| 0093630 | 11/1983 | European Pat. Off. . |
| 0214043 | 3/1987 | European Pat. Off. . |
| 2435790 | 2/1976 | Fed. Rep. of Germany . |
| 2574282 | 6/1986 | France . |
| 2070437 | 9/1981 | United Kingdom . |

*Primary Examiner*—Dalton L. Truluck

*Attorney, Agent, or Firm*—Fidelman & Wolffe

[57] ABSTRACT

An instrument of artificial insemination or embryo transfer by a transperitoneal and/or cervical route or for sampling follicular liquids in mammals especially horses, pigs, sheep, goats, deer and carnivores is of the type constituted by a syringe formed by a sheath in which slides in fluid-tight manner a piston movable in translation. The sheath is externally protected by a rigid cover and is immobilized in a manipulator sleeve comprising a rotary member adapted to actuate the piston. The anterior end of the sheath is fitted with a needle. The cover protecting the sheath is covered by and guides a palpator the length of which is greater than that of the cover but less than that of the sheath (including the needle). Thus the needle of the syringe is selectively covered or exposed in whole or in part by axial sliding movement of the cover.

22 Claims, 2 Drawing Sheets

INSTRUMENT FOR ARTIFICIAL INSEMINATION, EMBRYO TRANSFER OR SAMPLING FOLLICULAR LIQUIDS IN MAMMALS

BACKGROUND OF THE INVENTION

1. Field of the invention

The invention concerns an instrument for artificial insemination, embryo transfer or sampling follicular liquids in mammals in general and in horses, pigs, sheep, goats, cattle, deer and all carnivores in particular.

2. Description of the prior art

There are known laparoscopy techniques for "in situ" manipulation of the genital tract and the ovaries using instruments manipulated from outside the animal but inserted into the abdominal cavity through the opening in a trocar previously inserted through the skin and the peritoneum. This technique is employed when the neck of the uterus is difficult to pierce, as in goats, or even impossible to pierce, as in sheep and dogs. It is preferred over surgical intervention (laparotomy) which usually causes as a post-operative complication adherence of the broad ligament and/or of the peritoneum to the oviduct and/or the uterus and/or endometrial adhesions.

The invention is therefore concerned with an instrument that can be used for artificial insemination or embryo transfer by a transperitoneal route, for example in goats, sheep and dogs, or by the natural path where the morphology of the mammal lends itself to this. This instrument may also be applied to sampling follicular liquids by the cervical route.

There are already known (French patent application No. 85 12 386 of Aug. 14, 1985) syringes formed by a sheath and a piston translational movement of which is accurately controlled by a thumbwheel carried by a sleeve coupled to the anterior end of the sheath. In this embodiment the anterior end of the sheath is extended by a needle coupled to a plug comprising a conical cavity, this plug being adhesively bonded or welded to the inside of the anterior end of the sheath. It is then possible to use either a piston provided with a removable sealing head or (where the sheath encloses a fine sterilized packaging straw) the plunger stem itself, the piston head being in this case removed and replaced by the "factory" plug usually closing off the packaging straw.

The sheath is protected externally by a rigid cover or tubular plug preventing it deforming when it is inserted.

One object of the invention consists in improvements to this known instrument so that it may be used, especially in the transperitoneal technique, under the best possible handling and dosage control conditions, whether for artificial insemination or for embryo transfer.

Another object of the invention is to free one hand of the operator so that he can manipulate simultaneously the transfer instrument and the endoscope.

A final object of the invention is to mask the needle during the insertion of the instrument to avoid bruising, injuring or stressing the animal.

SUMMARY OF THE INVENTION

The invention consists in an instrument for artificial insemination or embryo trnasfer by a transperitoneal and/or cervical route in mammals or for sampling follicular liquids by the cervical route, of the kind constituted by a syringe formed by a sheath and a piston adapted to move in translation in the sheath in a fluid-tight way by sliding therein, a rigid cover protecting the exterior of the sheath, a manipulator sleeve in which the sheath is immobilized, a rotary member on the sleeve adapted to actuate the piston, a needle at an anterior end of the sheath, and a palpator which covers and is guided by the cover and has a length which is greater than that of the cover and less than the combined length of the sheath and the needle, whereby the needle of the syringe is selectively covered during insertion of the instrument or exposed in whole or in part when the instrument is positioned facing one of the two uterine horns by axial sliding movement of the cover.

In accordance with one characteristic feature of the invention and for the purpose of monitoring visually, by endoscopic means, the insemination or embryo transfer operation, an anterior end of the palpator comprises at least one graduated radial slot enabling movement of the piston within the sheath to be seen, the sheath being transparent to this end.

Other characteristics and advantages of the invention will emerge from the following description and the appended drawings.

FIGS. *2a* through *2d* are views in cross-section of the anterior part of the sheath equipped with needles of different sizes and shapes usable in particular for intervention by the cervical route.

Figure 3:
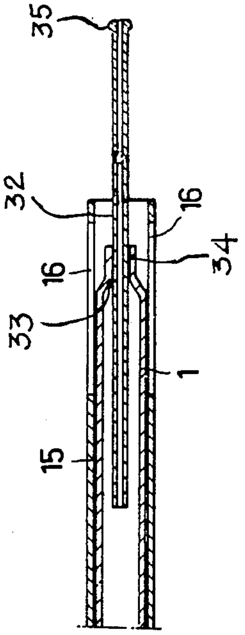

FIG. 3 is a view in longitudinal cross-section of the end of the sheath coupled to a semi-rigid needle in a plastics material intended for embryo transfer.

DESCRIPTION OF THE PREFERRED EMBODIMENTS

Figure 1:
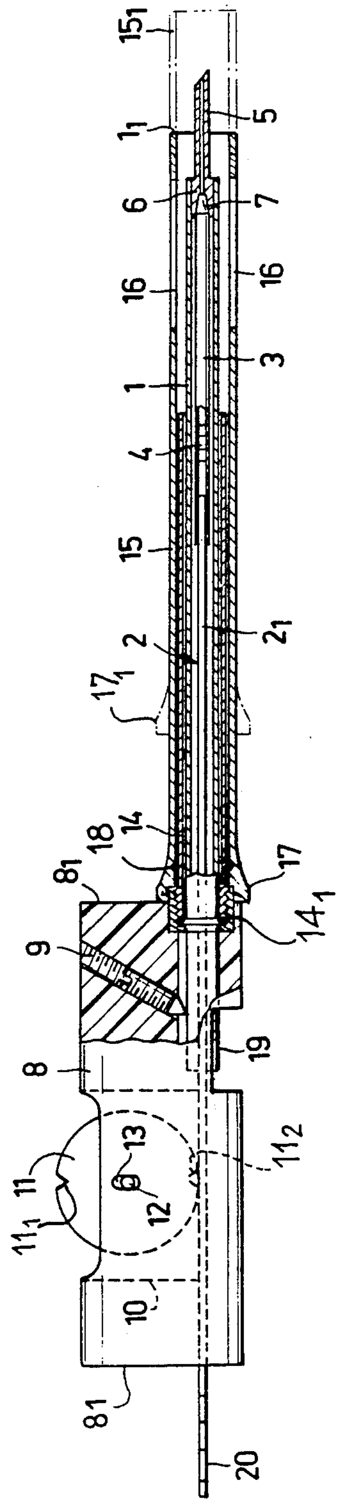
FIG. 1 is a view partly in longitudinal cross-section of the instrument in accordance with the invention, employing a fine semen packaging straw.

The instrument shown in FIG. 1 is constituted, in the known way, by a syringe formed by a semi-rigid sheath 1 made from a transparent, flexible and deformable plastics material in which moves in a fluid-tight way a piston 2 that is able to move to and fro in translation and the plunger stem $\mathbf{2}_1$ of which can optionally receive a removable head providing a seal with the bore in the sheath 1 or be used on its own, as in the example of FIG. 1 where a sterilized semen packaging straw 3 is used. In the example shown in FIG. *2a* only, the piston head $\mathbf{2}_2$ is formed by a cap crimped over the forward end of the plunger stem and comprising a rounded surface $\mathbf{2}_3$ merging with an annular lip $\mathbf{2}_4$ of greater diameter than its nominal diameter, this lip having a diameter slightly greater than that of the bore in the sheath 1 which deforms radially as the piston head moves along it. In this way an excellent seal without jamming is obtained within the sheath.

In the second case (FIG. 1) the plunger stem $\mathbf{2}_1$ bears directly on the "factory" plug 4 of the straw which then itself serves as the piston head. To this end the diameter of the plunger stem $\mathbf{2}_1$ is slightly greater than that of the passage inside the packaging straw 3 so that said stem can, by displacing the "factory" plug, expell the contents of said straw through the needle 5 which extends the sheath 1.

The needle is fastened to a plug 6 adhesively bonded or welded to the interior of the forward part of the sheath 1, said plug comprising a conical cavity 7 into which the anterior end of the straw 3 may be simply force-fitted. It is to be understood that the syringe may be used as previously stated, without any straw (especially where the semen used is fresh) and in this case the plunger stem $2_1$ is provided at its forward end with a removable piston head $2_2$ like that described hereinabove with reference to FIG. *2a.*

Also in the known way, the sheath 1 is fitted to a handle 8 for manipulating it, by means of a grub screw 9, for example, in such a way that it is immobilized in translation and in rotation.

The plunger stem $2_1$ projects from the posterior end of the sheath 1 and passes through the handle 8 to project from its rear surface $8_1$. The handle includes a cavity 10 in which is mounted free to rotate to and fro a thumbwheel 11 provided with at least two diametrally opposite notches $11_1$–$11_2$, the angular travel of 180° between these notches corresponding to a linear travel of the piston 2 equal to one half-dose, for the purpose of inseminating one uterine horn. The peripheral edge of the thumbwheel 11 is in contact with the plunger stem $2_1$ and the thumbwheel is advantageously mounted on a pin 12 housed in a vertical slot 13 enabling it to be pressed strongly against the plunger stem.

Finally, the sheath 1 is protected externally by a rigid cover 14 designed to protect the sheath 1, this cover extending over only part of the length of said sheath and screwing into the manipulator sleeve 8, after insertion of an O-ring seal $14_1$.

To adapt this instrument to the technique of artificial insemination and embryo transfer by the transperitoneal route, the syringe is enclosed in a palpator 15 that can slide freely in the axial direction on the cover 14 which serves as a guide for it. The length of the palpator is slightly less than that of the sheath (inclusive of the length of the needle 5) so that it is able to assume at least two distinct positions, on the one hand a so-called "syringe insertion" position (as shown in chain-dotted outline with the reference number $15_1$), in which case the needle 5 is covered by the palpator, and on the other hand a so-called "operational" position (as shown in full line with the reference number 15) in which case the needle 5 projects to a greater or lesser degree relative to the end $15_2$ of the palpator.

The palpator 15 advantageously comprises one or more graduated longitudinal slots 16 situated near the anterior part of the sheath 1, enabling displacement of the piston 2 by the thumbwheel 11 to be monitored by viewing it through the sheath. The end of the palpator is rounded off to avoid injuring the subject.

The palpator further comprises at its posterior end a tulip-shaped shoulder 17 which, when it is fully retracted, bears on the forward front surface $8_1$ of the handle 8. On the other hand, when the palpator is in the insertion phase ($15_1$), the shoulder 17 is moved away from this front surface $8_1$.

The palpator comprises at the position of its tulip-shaped shoulder 17 an O-ring seal 18 opposing passage of the gas that is usually blown into the space between the viscera and the abdominal wall of the subject during this type of procedure. This O-ring 18 consequently provides a perfect seal by closing off any lamellar interstices that might remain between the conduit in the palpator and the periphery of the stiffener cover 14.

In accordance with another characteristic feature of the invention, the handle 8 comprises a second notch 19 diametrally opposite the notched thumbwheel 11 on which the thumb is placed, this notch being designed to receive the index finger of the operator. The stem $2_1$ of the piston 2 may advantageously comprise at its posterior end one or more visual markers 20, once again to enable its linear travel to be monitored.

If this instrument is used by the transperitoneal route, two fine incisions are made in the abdominal wall of the animal, one receiving the sleeve of a trocar into the aperture in which an endoscope will be inserted, while the other receives a second trocar intended to serve as a guide for the syringe in accordance with the invention. It is to be understood that the diameter of the aperture in this second trocar corresponds substantially to that of the palpator 15 but that its length is less than that of the latter so that the graduated viewing windows 16 which make it possible to monitor the travel of the piston 2 and thus the precise dosage of the semen or medium are not masked. When the second trocar is fitted, the operator inserts the syringe into the aperture in the trocar, taking care to hold the palpator in the position denoted $15_1$, that is to say in the insertion phase in which the needle 5 is covered. The palpator is held with one hand only, the operator placing his thumb on the thumbwheel 11 and his index finger in the holding notch 19, while the ring finger and the little finger are placed one on each side of the tulip-shaped shoulder 17.

Once the syringe is in place, the operator slides the palpator back in the axial direction, optionally until the shoulder 17 butts up against the front surface $8_1$ of the handle 8. In this position the needle 5 projects to a greater or lesser degree relative to the forward end of the palpator 15. It then remains only to pierce the uterine horn and then to inject the semen or transfer the embryos, by simple rotation of the thumbwheel 11 which causes linear displacement of the piston 2 in the sheath 1 or in the packaging straw 3. The travel of the piston is monitored either by means of the marker or markers 20 provided at its rear end or by sighting through the graduated viewing window 16, such sighting being facilitated by the illumination provided by the endoscope.

In the embodiment shown in FIG. 1, the needle 5 is adapted to pierce the uterine horn. It is therefore made of metal, tapered and bevelled (with three flats) so that, with a single, gentle thrust, it can be passed through the wall of the uterine horn or the membrane of the follicle. The syringes shown in FIGS. *2a* through *2d* are more specifically intended for artificial insemination, embryo transfer and sampling of follicular liquids by the natural route, that is to say by the cervical route, which is faster, easier, less stressful and less costly than laparoscopy techniques.

The sheath shown in FIG. *2a* comprises, as in FIG. 1, a plug 6 and a metal needle 5, the plug being housed in the anterior part of the sheath 1 and fixed by adhesive bonding or ultrasonic welding. The needle 5 is protected externally, during transport, by a protective skirt 21 in the form of a section of tube coaxial with and exterior to the needle 5. Note that the plug 6 comprises internally a conical cavity 7 for optionally receiving a packaging straw, this cavity merging with the passage $5_1$ in the needle without any sharp corners to avoid possible bruising of the embryo.

In the example shown in FIG. *2a* only, the piston is constituted by the plunger stem $2_1$ the forward end of which is covered by the piston head $2_2$ which is in the form of a cap whose forward front surface $2_3$ is rounded, merging with the nominal diameter of the cap $2_2$ through an annular lip $2_4$ providing the seal with the bore in the sheath 1. The sheath is deliberately made from a flexible and deformable material so that it is deformed slightly by the annular lip $2_4$ as the latter moves along it. Finally, the forward edge $1_1$ of the sheath 1 merging with the metal needle 5 is covered by a ring 22 molded in one piece with the plug and eliminating any sharp corners on the sheath in order to avoid injuring the animal during insertion of the instrument.

Figure 2A:
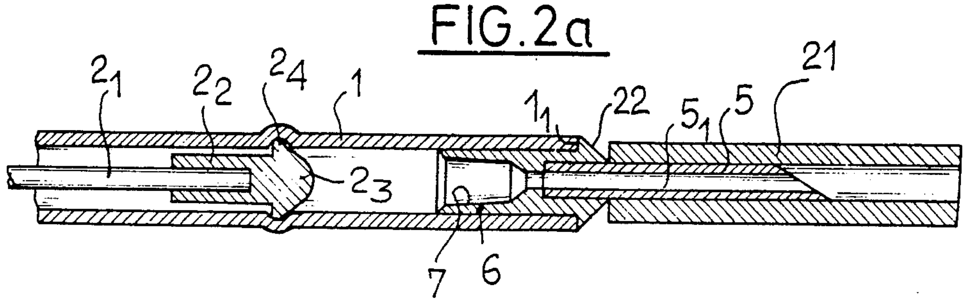
Figure 2B:
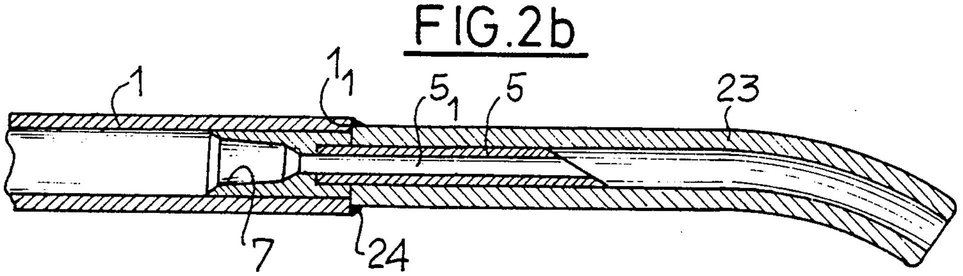

In FIG. 2*b* the metal needle 5 is extended by a second, coaxial and external tube 23 adhesively bonded or ultrasonically welded to the forward edge $1_1$ of the sheath. The metal needle 5 serves to support and guide the tube 23 whose insertion end $23_1$ is rounded off to avoid injury. Once again the passage in the metal needle 5 merges with the frustoconical cavity 7 in the plug 6 without any sharp corners to avoid any injury to the embryos. Finally, a molded ring 24 covers the sharp corner at the forward end of the sheath. The tube 23 may be made from a rigid plastics material or metal and may be curved as and when required, that is to say at the time of use, to suit the instrument to the morphology of the animal. This type of syringe is used in particular for embryo transfer by the cervical route and for artificial insemination by laparoscopy. It is, moreover, perfectly suitable for use on human females.

Figure 2C:
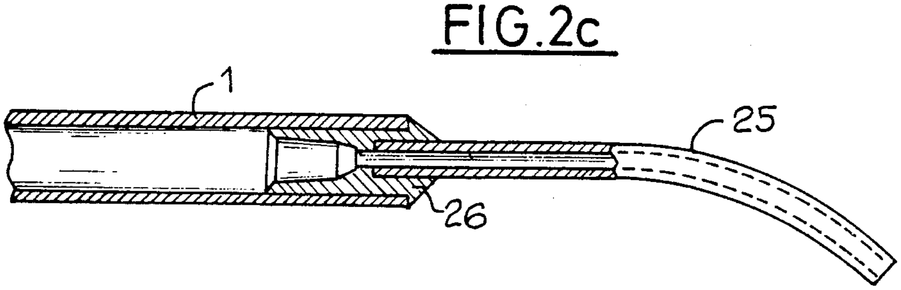

FIG. 2*c* is comparable to FIG. 2*b* in all respects except that the metal needle 5 is eliminiated and a tube 25 is fixed directly into the plug 6. The tube 25 may be made from Delrin or metal and once again will be curved as and when required according to the species of animal to be treated. To avoid injuring the animal the forward end of the tube is rounded off and the sharp corner on the forward section of the sheath is masked by a ring 26 molded in one piece with the plug 6.

Figure 2D:
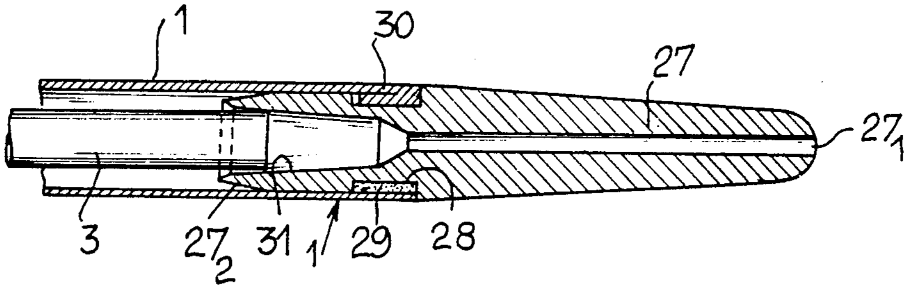

In FIG. 2*d* the needle is particularly intended for artificial insemination of goats and deer by the cervical route and comprises a one-piece plug 27 of slightly tapering shape the operative end $27_1$ of which is substantially hemispherical. This needle 27 comprises an annular groove 28 for fixing the sheath 1. The needle/sheath joint may be made either by a reservoir of adhesive 29 inserted into the annular groove 28 or by shaping the anterior end 30 of the sheath into a form resembling a hairpin-type clip.

The portion of the needle 27 inserted into the sheath 1 is slightly reduced in diameter and tapered at the end, to favor the passage of the sheath, as visible at $27_2$. Also, this portion of the needle resembles the plug 6 of FIGS. 2*a* through 2*c* and comprises a frustoconical cavity 31 adapted to receive a packaging straw 3. As in FIGS. 2*a* through 2*c*, the plug is flared at $27_3$ to favor insertion of the straw. Finally, the portion of the needle situated beyond the sheath is slightly tulip-shaped so as to merge with the diameter of said sheath and consequently avoid any projecting corners that could injure or stress the animal. It is to be understood that where the trumps 23, 25 and 27 are made from a plastics material, use is made of non-toxic materials having some rigidity but able to be curved to suit the morphology of the animal.

In FIG. 3 the needle 5 is semi-rigid and is made as an extruded capillary tube 32 extending into the anterior end of the sheath 1. This capillary tube extends into the sheath 1 over a length substantially equal to that by which it extends out of said sheath. To this end the end of the sheath comprises a restriction 33 to match the diameter of the capillary tube 32 which is adhesively bonded or sealed at 34 to the interior of the restriction 33. The needle 32 comprises at its forward end a swelling 35 forming a sort of head having at least two functions, one of which is to blunt the needle to prevent it injuring or stressing the animal and the other of which is to prevent the embryo from being sucked out. This type of needle is more specifically intended for embryo transfer as the capillary tube, by virtue of its fineness and its length, is particularly well adapted to opposing loss of embryos. The embryo usually being trapped between two air bubbles in its "middle", the use of a capillary tube is more secure. The capillary tube used here is of small diameter (in the order of a few tenths of a millimeter) and its length of approximately 10 to 15 cm is precisely sufficient to avoid loss of the embryo. Moreover, the capillary tube 32 is made from a non-toxic transparent type plastics material which provides for good visual inspection of the embryo before and after transfer.

This needle is used with the instrument shown in FIG. 1 and is of course masked by the palpator 15 during its insertion through the aperture in the trocar. The only difference lies in the fact that, because it is not tapered, to enable it to be inserted into the uterine horn it is necessary to use another trocar to make a fine incision in the wall of the uterine horn in order to be able to insert the head 35 into it. The external length of the capillary tube is such that the embryo or embryos may easily be deposited several centimeters beyond the incision, which results in improved implantation of the embryo.

When the instrument is removed, the head 35 tends to close the small incision in the uterine horn and thus to oppose sucking out of the embryo. This instrument cannot, of course, be used with a packaging straw because of the portion of the capillary tube projecting into the sheath 1. The embryo (or each embryo) is consequently sucked up from a Petri dish by moving the piston 2 fitted with its sealing head $2_2$ for transfer under the conditions described hereinabove. Thus this semi-rigid needle 32 enables deep deposition of the embryo in the uterine horns, beyond the incision (5 cm) without surgery.

The instrument as described and shown in the various embodiments has numerous advantages since it can not only be used for artificial insemination, embryo transfer or sampling of follicular liquids, but also frees completely one hand of the operator who can simultaneously maneuvre the notched thumbwheel 11 with his thumb, hold the handle by means of the notch 19 and maneuvre the palpator by its shoulder 17, held between the ring finger and the little finger. In the case of laparoscopy, the free hand can orient the endoscope to enable correct positioning of the needle on the uterine horn to be treated. Moreover, the palpator 15 sliding in the opening in the trocar is perfectly guided which makes it possible to achieve great precision in positioning the instrument. Finally, the palpator makes it possible to inspect the viscera, to check the number and quality of the follicles on each ovary, to position the uterine horns (artificial insemination) and then to pierce, inseminate, transfer or sample the follicular liquid to recover the ovocytes in a precisely controlled way. The graduated viewing slots 16 enable continuous monitoring of the position of the piston 2 and consequently continuous monitoring of the dosing of the semen or the expulsion of the embryos.

Finally, the needle may of course be covered with a protective cap for reasons of hygiene.

We claim:

1. An instrument for artificial insemination or embryo trannsfer by a transperitoneal and/or cervical route or for sampling follicular liquids in mammals, comprising:

- a hollow tubular sheath;
- a piston movable in said sheath in an axial direction of the sheath and forming a fluid-tight seal within the sheath;
- a rigid cover extending around the outer circumference of the sheath and along at least a part of the length of the sheath;
- a needle attached to an anterior end of the sheath and extending past the anterior end of the sheath;
- a handle attached to a posterior end of said sheath;
- a rotary member located on said handle which cooperates with the piston so as to move the piston in the axial direction when the rotary member is rotated;
- a palpator extending around the outer circumference of the cover, said palpator having a length which is greater than the length of the cover, but is less than the combined length of the sheath and the needle, said palpator being movable in the axial direction and being guided by said cover between a covered position where an anterior end of the palpator extends past an end of the needle, and an exposed position where the end of the needle extends past the anterior end of the palpator.

2. Instrument according to claim 1, wherein an anterior end of said palpator is rounded off and comprises at least one radial slot constituting a graduated viewing window for monitoring movement of said piston in said sheath.

3. Instrument according to claim 1, wherein a posterior end of said palpator comprises a tulip-shaped maneuvering shoulder which, when said palpator is in the exposed position, butts against an anterior surface of said handle.

4. Instrument according to claim 1, wherein said rotary member projects out from an upper surface of the handle for manipulation by an operator, and said handle comprises a positioning notch for the operator in a lower surface thereof.

5. Instrument according to claim 1, further comprising an O-ring seal located between a posterior end of the palpator and the outside circumference of said cover surrounding said sheath.

6. Instrument according to claim 1, wherein said piston comprises a stem that projects beyond a posterior end of said handle, said stem comprising one or more index markings for monitoring its linear travel.

7. Instrument according to claim 1, wherein said sheath is made from a flexible, deformable, transparent, non-toxic plastics material.

8. Instrument according to claim 1, further comprising an adhesively bonded or welded plug located within said sheath, wherein said needle is fixed into an anterior end of said plug.

9. Instrument according to claim 8, wherein said plug has a conical cavity located at a posterior end thereof, and further comprising a sterilized straw used to package semen or embryos located in said sheath with one end thereof received in said conical cavity.

10. Instrument according to claim 1, wherein said needle is of metal and bevelled with three flats.

11. Instrument according to claim 10, further comprising a removable skirt whereby said needle is protected during transportation.

12. Instrument according to claim 1, further comprising a tube located around the outer circumference of said needle and extending past an anterior end of said needle, an anterior end of said tube being rounded off.

13. Instrument according to claim 1, wherein said needle is made from a semi-rigid plastics material and is adapted to be curved to shape as and when required according to the morphology of the animal.

14. Instrument according to claim 1, further comprising an adhesively bonded or welded plug located within said sheath, wherein said needle is fixed into an anterior end of said plug, and wherein said needle and said plug form an integral member, said integral member comprising an annular groove for securing the member to the anterior end of said sheath, the part of the situated beyond said groove being flared so as to merge with the outer circumference of said sheath.

15. Instrument according to claim 14, wherein said sheath is fixed to said member by adhesive bonding or ultrasonic welding.

16. Instrument according to claim 14, wherein the anterior end of said sheath comprises a hairpin-shaped rim accommodated in said groove in said member.

17. Instrument according to claim 14, wherein a rear portion of said member, situated inside said sheath, is slightly reduced in diameter and tapered and comprises a frustoconical cavity merging without sharp corners with a passage through said needle.

18. Instrument according to claim 1, wherein said piston comprises a plunger stem and a removable sealing head attached to an anterior end of the plunger stem and having a rounded front surface merging with an annular sealing lip which deforms said flexible sheath as it moves in the axial direction.

19. Instrument according to claim 1, further comprising an adhesively bonded or welded plug located in said sheath which receives said needle, wherein said plug comprises, molded integrally therewith, a ring covering an anterior edge of said sheath.

20. Instrument according to claim 1, wherein said needle is non-toxic and is formed from flexible capillary tube extending past the anterior end of said sheath and extending a predetermined distance into the interior of the sheath, an anterior end of said capillary tube comprising a head of increased diameter.

21. Instrument according to claim 20, wherein said anterior end of said sheath comprises a restriction located therein into which said capillary tube is adhesively bonded or welded.

22. Instrument according to claim 1, wherein said rotary member comprises two diametrically opposed notches, and wherein rotating said rotary member 180° corresponds to the injection of one half-dose of semen.

* * * * *

UNITED STATES PATENT AND TRADEMARK OFFICE
CERTIFICATE OF CORRECTION

PATENT NO. : 4,846,785

DATED : July 11, 1989

INVENTOR(S) : Robert CASSOU et al.

It is certified that error appears in the above-identified patent and that said Letters Patent is hereby corrected as shown below:

On the title page:

In block [21], change Appl. No. "71,459" to Appl. No. --145,997--.

At column 3, line 29, change "sleeve 8" to --handle 8--.

At column 5, line 57, change "trumps" to --tubes--.

Signed and Sealed this

Fifth Day of June, 1990

*Attest:*

HARRY F. MANBECK, JR.

*Attesting Officer*

*Commissioner of Patents and Trademarks*